US012616582B2

(12) United States Patent
Stiefferman et al.

(10) Patent No.: US 12,616,582 B2
(45) Date of Patent: May 5, 2026

(54) EXPANDABLE INTERBODY SPACER FOR SPINAL FUSION

(71) Applicant: CoreLink, LLC, Fenton, MO (US)

(72) Inventors: Tim Stiefferman, House Springs, MO (US); Josh Arnone, St. Charles, MO (US)

(73) Assignee: CORELINK, LLC, St. Louis, MO (US)

( * ) Notice: Subject to any disclaimer, the term of this patent is extended or adjusted under 35 U.S.C. 154(b) by 460 days.

(21) Appl. No.: 17/986,786

(22) Filed: Nov. 14, 2022

(65) Prior Publication Data

US 2023/0277330 A1     Sep. 7, 2023

Related U.S. Application Data

(60) Provisional application No. 63/263,972, filed on Nov. 12, 2021.

(51) Int. Cl.
*A61F 2/44* (2006.01)
*A61F 2/30* (2006.01)

(52) U.S. Cl.
CPC .... *A61F 2/447* (2013.01); *A61F 2002/30481* (2013.01); *A61F 2002/30556* (2013.01); *A61F 2002/30579* (2013.01)

(58) Field of Classification Search
None
See application file for complete search history.

(56) References Cited

U.S. PATENT DOCUMENTS

| | | | |
|---|---|---|---|
| 4,863,476 | A | 9/1989 | Shepperd |
| 5,554,191 | A | 9/1996 | Lahille et al. |
| 5,653,763 | A | 8/1997 | Errico et al. |
| 5,665,122 | A | 9/1997 | Kambin |
| 6,045,579 | A | 4/2000 | Hochschuler et al. |
| 6,080,193 | A | 6/2000 | Hochschuler et al. |
| 6,176,882 | B1 | 1/2001 | Biedermann et al. |
| 6,368,351 | B1 | 4/2002 | Glenn et al. |
| 6,443,989 | B1 | 9/2002 | Jackson |
| 6,576,016 | B1 | 6/2003 | Hochshuler et al. |
| 6,685,742 | B1 | 2/2004 | Jackson |
| 7,569,074 | B2 | 8/2009 | Eisermann et al. |
| 7,655,046 | B2 | 2/2010 | Dryer et al. |
| 7,828,849 | B2 | 11/2010 | Lim |
| 8,062,375 | B2 | 11/2011 | Glerum et al. |

(Continued)

*Primary Examiner* — Jan Christopher L Merene
(74) *Attorney, Agent, or Firm* — Stinson LLP

(57) ABSTRACT

An expandable interbody spacer for spinal fusion includes opposing upper and lower end plates. An actuator moves the upper and lower end plates heightwise relative to one another to expand the height of the expandable interbody spacer. An end plate fastener secures the upper and lower end plates to one another and enables the upper and lower end plates to heightwise move relative to one another. The upper and lower end plates and the at least one end plate fastener are integrally formed as a single, one-piece, monolithic component. An expandable interbody space may include upper and lower end plates with overlapping anterior and posterior walls that define openings in communication with an internal chamber. An expandable interbody spacer may include a barrel nut defining a window to enable bone graft to pass therethrough and into an internal chamber.

16 Claims, 16 Drawing Sheets

(56) References Cited

U.S. PATENT DOCUMENTS

| | | | |
|---|---|---|---|
| 8,105,382 B2 | 1/2012 | Olmos et al. | |
| 8,133,232 B2 | 3/2012 | Levy et al. | |
| 8,366,777 B2 | 2/2013 | Matthis et al. | |
| 8,382,842 B2 | 2/2013 | Greenhalgh et al. | |
| 8,398,713 B2 | 3/2013 | Weiman | |
| 8,435,298 B2 | 5/2013 | Weiman | |
| 8,518,120 B2 | 8/2013 | Glerum et al. | |
| 8,568,481 B2 | 10/2013 | Olmos et al. | |
| 8,579,981 B2 | 11/2013 | Lim et al. | |
| 8,603,170 B2 | 12/2013 | Cipoletti et al. | |
| 8,628,577 B1 | 1/2014 | Jimenez | |
| 8,632,595 B2 | 1/2014 | Weiman | |
| 8,679,183 B2 | 3/2014 | Glerum et al. | |
| 8,685,095 B2 | 4/2014 | Miller et al. | |
| 8,795,366 B2 | 8/2014 | Varela | |
| 8,845,731 B2 | 9/2014 | Weiman | |
| 8,845,734 B2 | 9/2014 | Weiman | |
| 8,864,833 B2 | 10/2014 | Glerum et al. | |
| 8,888,854 B2 | 11/2014 | Glerum et al. | |
| 8,940,049 B1 | 1/2015 | Jimenez et al. | |
| 8,986,389 B2 | 3/2015 | Lim et al. | |
| 9,039,771 B2 | 5/2015 | Glerum et al. | |
| 9,119,730 B2 | 9/2015 | Glerum et al. | |
| 9,211,196 B2 | 12/2015 | Glerum et al. | |
| 9,271,846 B2 | 3/2016 | Lim et al. | |
| 9,320,610 B2 | 4/2016 | Alheidt et al. | |
| 9,358,128 B2 | 6/2016 | Glerum et al. | |
| 9,358,129 B2 | 6/2016 | Weiman | |
| 9,370,434 B2 | 6/2016 | Weiman | |
| 9,421,110 B2 | 8/2016 | Masson et al. | |
| 9,421,111 B2 | 8/2016 | Baynham | |
| 9,452,063 B2 | 9/2016 | Glerum et al. | |
| 9,463,099 B2 | 10/2016 | Levy et al. | |
| 9,474,625 B2 | 10/2016 | Weiman | |
| 9,486,328 B2 | 11/2016 | Jimenez et al. | |
| 9,492,287 B2 | 11/2016 | Glerum et al. | |
| 9,492,288 B2 | 11/2016 | Wagner et al. | |
| 9,498,349 B2 | 11/2016 | Patterson et al. | |
| 9,510,954 B2 | 12/2016 | Glerum et al. | |
| 9,539,108 B2 | 1/2017 | Glerum et al. | |
| 9,549,824 B2 | 1/2017 | Mcafee | |
| 9,561,116 B2 | 2/2017 | Weiman et al. | |
| 9,662,224 B2 * | 5/2017 | Weiman | A61F 2/4455 |
| 9,668,879 B2 | 6/2017 | Jimenez et al. | |
| 9,750,617 B2 | 9/2017 | Lim et al. | |
| 9,801,734 B1 | 10/2017 | Stein et al. | |
| 9,833,337 B2 | 12/2017 | Hleihil et al. | |
| 9,855,151 B2 | 1/2018 | Weiman | |
| 9,867,717 B2 | 1/2018 | Jimenez | |
| 9,931,226 B2 | 4/2018 | Michna et al. | |
| 9,956,087 B2 | 5/2018 | Seifert et al. | |
| 9,987,144 B2 | 6/2018 | Seifert et al. | |
| 10,016,282 B2 | 7/2018 | Seifert et al. | |
| 10,034,772 B2 | 7/2018 | Glerum et al. | |
| 10,052,214 B2 | 8/2018 | Jimenez et al. | |
| 10,080,669 B2 | 9/2018 | Davenport et al. | |
| 10,098,759 B2 | 10/2018 | Weiman | |
| 10,137,001 B2 | 11/2018 | Weiman | |
| 10,188,527 B2 | 1/2019 | Rogers et al. | |
| 10,201,431 B2 | 2/2019 | Slater et al. | |
| 10,219,914 B2 | 3/2019 | Faulhaber | |
| 10,226,359 B2 | 3/2019 | Glerum et al. | |
| 10,265,191 B2 | 4/2019 | Lim et al. | |
| 10,350,081 B2 | 7/2019 | Seifert et al. | |
| 10,363,142 B2 | 7/2019 | Mcclintock et al. | |
| 10,376,377 B2 | 8/2019 | Seifert et al. | |
| 10,390,962 B2 | 8/2019 | Weiman | |
| 10,390,963 B2 | 8/2019 | Olmos et al. | |
| 10,398,566 B2 | 9/2019 | Olmos et al. | |
| 10,492,924 B2 | 12/2019 | Stein et al. | |
| 10,524,924 B2 | 1/2020 | Davenport et al. | |
| 10,548,743 B2 | 2/2020 | Faulhaber | |
| 10,583,015 B2 | 3/2020 | Olmos et al. | |
| 10,624,761 B2 | 4/2020 | Davenport et al. | |
| 10,639,165 B2 | 5/2020 | Suh et al. | |
| 10,687,961 B1 | 6/2020 | Abdelgany et al. | |
| 10,687,963 B2 | 6/2020 | Jimenez et al. | |
| 11,033,403 B2 | 6/2021 | Predick et al. | |
| 11,045,326 B2 | 6/2021 | Seifert et al. | |
| 11,291,554 B1 * | 4/2022 | Prevost | A61F 2/30749 |
| 11,918,484 B2 * | 3/2024 | To | A61F 2/4611 |
| 12,138,179 B2 * | 11/2024 | Predick | A61F 2/30 |
| 2003/0236520 A1 | 12/2003 | Lim et al. | |
| 2006/0022180 A1 * | 2/2006 | Selness | A47B 91/028 254/104 |
| 2006/0247770 A1 | 11/2006 | Peterman | |
| 2008/0140207 A1 * | 6/2008 | Olmos | A61F 2/4455 623/17.11 |
| 2008/0183204 A1 * | 7/2008 | Greenhalgh | A61B 17/8858 606/198 |
| 2009/0222100 A1 * | 9/2009 | Cipoletti | A61F 2/447 606/90 |
| 2010/0082109 A1 * | 4/2010 | Greenhalgh | A61F 2/447 623/17.15 |
| 2010/0185291 A1 * | 7/2010 | Jimenez | F16F 1/025 623/17.16 |
| 2013/0211526 A1 * | 8/2013 | Alheidt | A61F 2/442 623/17.16 |
| 2013/0231747 A1 | 9/2013 | Olmos et al. | |
| 2014/0031938 A1 * | 1/2014 | Lechmann | A61F 2/442 623/17.16 |
| 2016/0038305 A1 * | 2/2016 | Weiman | A61F 2/30767 623/17.16 |
| 2016/0082109 A1 | 3/2016 | Gagliardi et al. | |
| 2017/0100255 A1 | 4/2017 | Hleihil et al. | |
| 2017/0100257 A1 | 4/2017 | Weiman et al. | |
| 2017/0290675 A1 | 10/2017 | Olmos et al. | |
| 2017/0290677 A1 | 10/2017 | Olmos et al. | |
| 2019/0000640 A1 | 1/2019 | Weiman | |
| 2019/0021868 A1 | 1/2019 | Ludwig et al. | |
| 2019/0274836 A1 * | 9/2019 | Eisen | A61F 2/4425 |
| 2019/0274837 A1 * | 9/2019 | Eisen | A61F 2/4611 |
| 2019/0336300 A1 | 11/2019 | Bernard et al. | |
| 2020/0138591 A1 | 5/2020 | Moskowitz et al. | |
| 2021/0205091 A1 * | 7/2021 | Hyeon | A61F 2/447 |
| 2023/0018019 A1 * | 1/2023 | Protopsaltis | A61F 2/4455 |

* cited by examiner

EXPANDABLE INTERBODY SPACER FOR SPINAL FUSION

CLAIM OF PRIORITY

This application claims the benefit of U.S. Provisional Patent Application Ser. No. 63/263,972, filed on Nov. 12, 2021, the entire content is hereby incorporated by reference.

FIELD OF THE DISCLOSURE

The present disclosure generally relates to an expandable interbody spacer for spinal fusion.

BACKGROUND OF THE DISCLOSURE

Spinal fusion is a surgical procedure used to correct problems with vertebrae of the spine. Spinal fusion fuses together the painful vertebrae so that they heal into a single, solid bone. In one method, the intervertebral disc between two vertebrae is removed and a small interbody spacer, also known as a cage, is inserted between the vertebrae. These interbody spacers usually enable bone graft material to be received therein to promote bone healing and facilitate the fusion. After the interbody spacer is inserted, surgeons often use metal screws, plates, and rods to further stabilize the spine.

SUMMARY OF THE DISCLOSURE

In one aspect, an expandable interbody spacer for spinal fusion generally comprises upper and lower end plates opposing one another and defining an internal chamber therebetween sized to receive bone graft therein. A distance between the upper and lower end plates defines a height of the expandable interbody spacer. An actuator is disposed between the upper and lower end plates. The actuator is configured to move the upper and lower end plates heightwise relative to one another to expand the height of the expandable interbody spacer. At least one end plate fastener secures the upper and lower end plates to one another and enables the upper and lower end plates to move heightwise relative to one another. The upper and lower end plates and the at least one end plate fastener are integrally formed as a single, one-piece, monolithic component.

In another aspect, an expandable interbody spacer for spinal fusion generally comprises upper and lower end plates opposing one another and defining an internal chamber therebetween sized to receive bone graft therein. A distance between the upper and lower end plates defines a height of the expandable interbody spacer. An actuator is disposed between the upper and lower end plates. The actuator is configured to move the upper and lower end plates heightwise relative to one another to expand the height of the expandable interbody spacer. The actuator comprises: a drive screw including a threaded portion, the drive screw being selectively rotatable about its axis; and at least one barrel nut comprising an internally threaded portion threaded on the screw drive. Rotation of the drive screw imparts translation of the at least one barrel nut along the drive screw and relative to the upper and lower implants to impart heightwise movement of the upper and lower end plates relative to one another. The at least one barrel nut includes a first longitudinal portion and a second longitudinal portion. The internally threaded portion is disposed between the first and second longitudinal portions. The first longitudinal portion defines a window to enable bone graft to pass therethrough and into the internal chamber.

In yet another aspect, an expandable interbody spacer for spinal fusion generally comprises upper and lower end plates opposing one another and defining an internal chamber therebetween sized to receive bone graft therein. A distance between the upper and lower end plates defines a height of the expandable interbody spacer. An actuator is disposed between the upper and lower end plates. The actuator is configured to move the upper and lower end plates heightwise relative to one another to expand the height of the expandable interbody spacer. Each of the upper and lower end plates includes opposite anterior and posterior walls. Overlapping portions of the anterior walls of the upper and lower end plates overlap and are in in opposing relationship. Overlapping portions of the posterior walls of the upper and lower end plates overlap and are in opposing relationship. The overlapping portions of each of the anterior and posterior walls of the upper and lower end plates define openings therethrough that are in communication with the internal chamber to enable bone growth.

DETAILED DESCRIPTION OF THE DISCLOSURE

Figure 1:
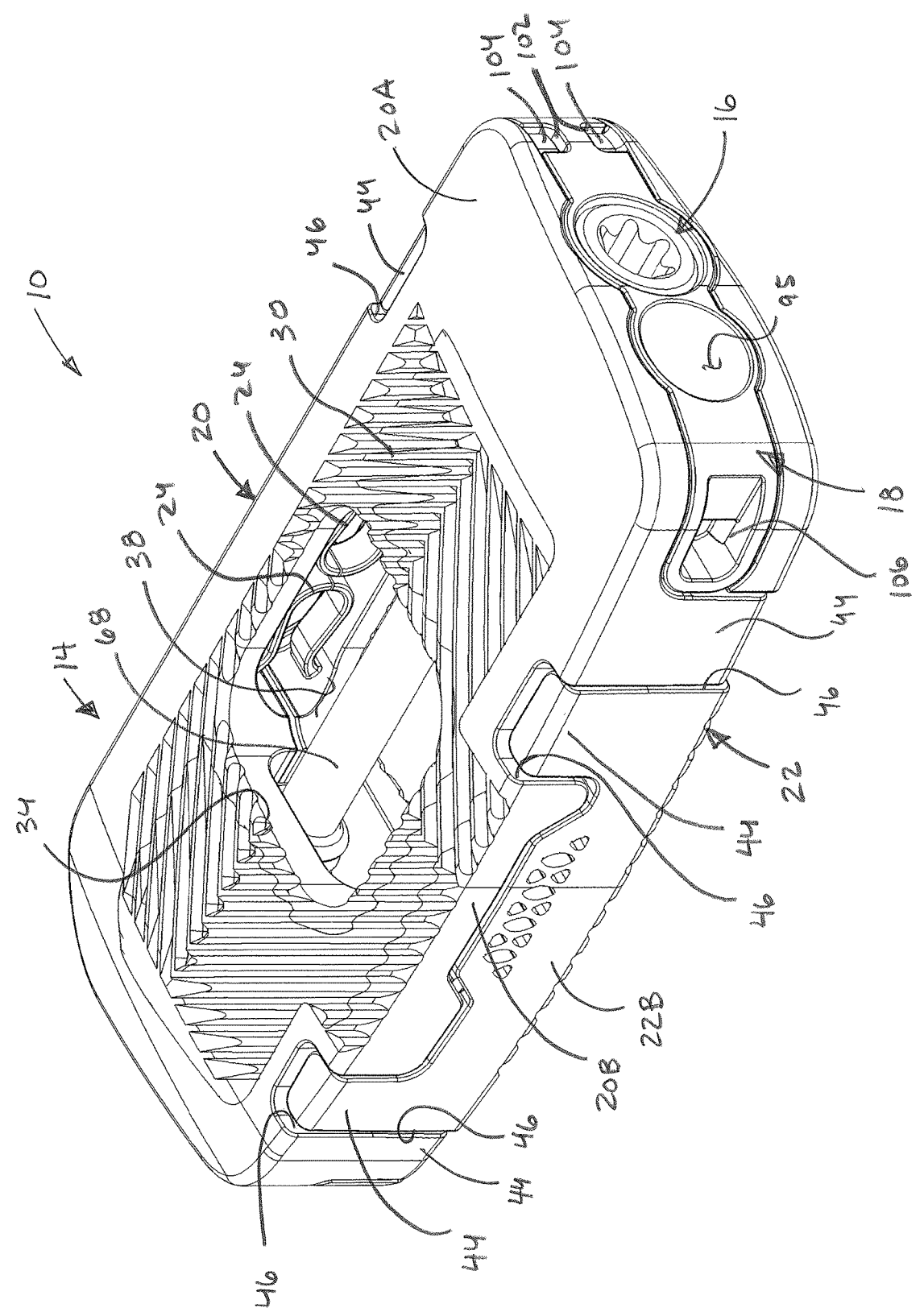
FIG. 1 is a front perspective of a one embodiment of an expandable interbody spacer, the interbody spacer being in a collapsed configuration.
Figure 2:
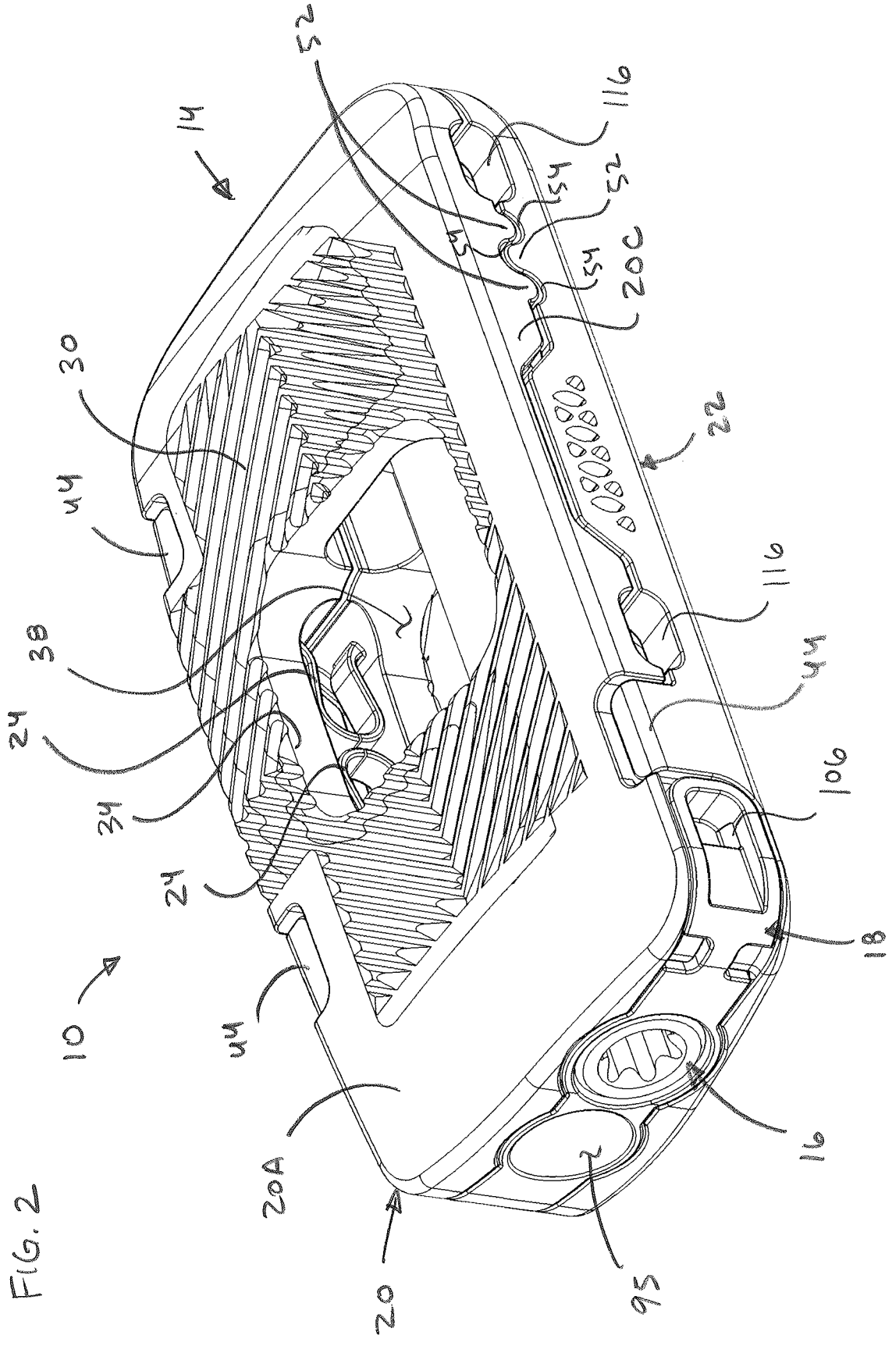
FIG. 2 is a rear perspective of the expandable interbody spacer.

Referring to FIG. 1, one embodiment of an expandable interbody spacer constructed according to the teachings of the present disclosure is generally indicated at reference numeral 10. The illustrated interbody spacer 10 is designed and constructed as a lateral interbody spacer for use in lateral lumbar interbody fusion (LLIF) or extreme lateral interbody fusion (XLIF) surgical procedures. It is understood that certain features and teachings of the present disclosure may apply to interbody spacers for other types of interbody fusion surgical procedures, such as but not limited to, posterior lumbar interbody fusion (PLIF), anterior lumbar interbody fusion (ALIF), and transforaminal lumbar interbody fusion (TLIF). The interbody spacer 10 has upper and lower surfaces (e.g., superior and inferior surfaces when implanted), front and rear sides (e.g., posterior and anterior sides when implanted, left and right ends (e.g., medial or leading and lateral or trailing ends during implantation), a height H extending between the upper and lower surfaces (e.g., inferior/superior dimension when implanted), a length L extending between the left and right ends (e.g., medial/lateral dimension when implanted), and a width W extending between the front and rear sides (e.g., anterior/posterior dimension when implanted).

The expandable interbody spacer 10 generally includes a spacer shell or casing, generally indicated at reference numeral 14, configured to be expandable heightwise (i.e., a generally superior/inferior direction when implanted); an actuator, generally indicated at reference numeral 16, configured to impart expansion of the spacer casing; and a coupling, generally indicated at reference numeral 18.

The spacer casing 14 includes upper and lower endplates, generally indicated at 20, 22, respectively, and one or more fasteners (shown best in FIGS. 1, 2, 9, and 10), each indicated at reference numeral 24, coupling the upper and lower end plates to one another. The upper and lower end plates 20, 22 are movable away from one another in the heightwise direction to expand the spacer casing 14. As explained in more detail below, the fastener(s) 24 secure the end plates 20, 22 to one another while enabling the end plates to be moved away from one another in the heightwise direction. In the illustrated embodiment, the upper and lower end plates 20, 22 and the fastener(s) 24 are integrally formed as a single, one-piece, monolithic construction. For example, the upper and lower end plates 20, 22 and the fastener(s) 24 may be formed as a single, one-piece, monolithic construction by additive manufacturing. This allows for ease of manufacture and the ability to construct the interbody spacer 10 without a frame or a spacer body surrounding the upper and lower endplates 20, 22 needed to maintain the upper and lower endplates attached to one another, as taught by the prior art. A suitable material for the upper and lower end plates 20, 22 and the fastener(s) 24 is titanium, although other biocompatible material may be used. It is understood that the upper and lower end plates 20, 22 and the fastener(s) 24 may not be formed as a single, one-piece construction.

Figure 7:
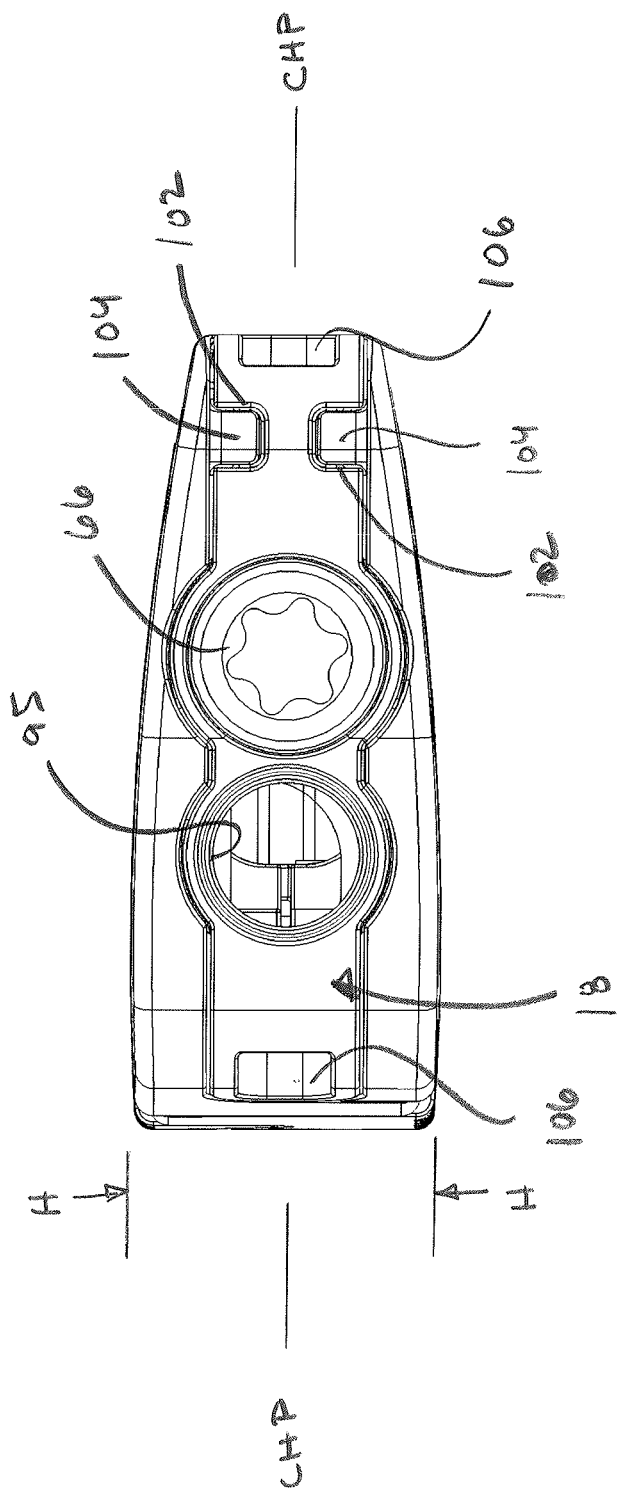
FIG. 7 is right elevational view of the expandable interbody spacer.
Figure 8:
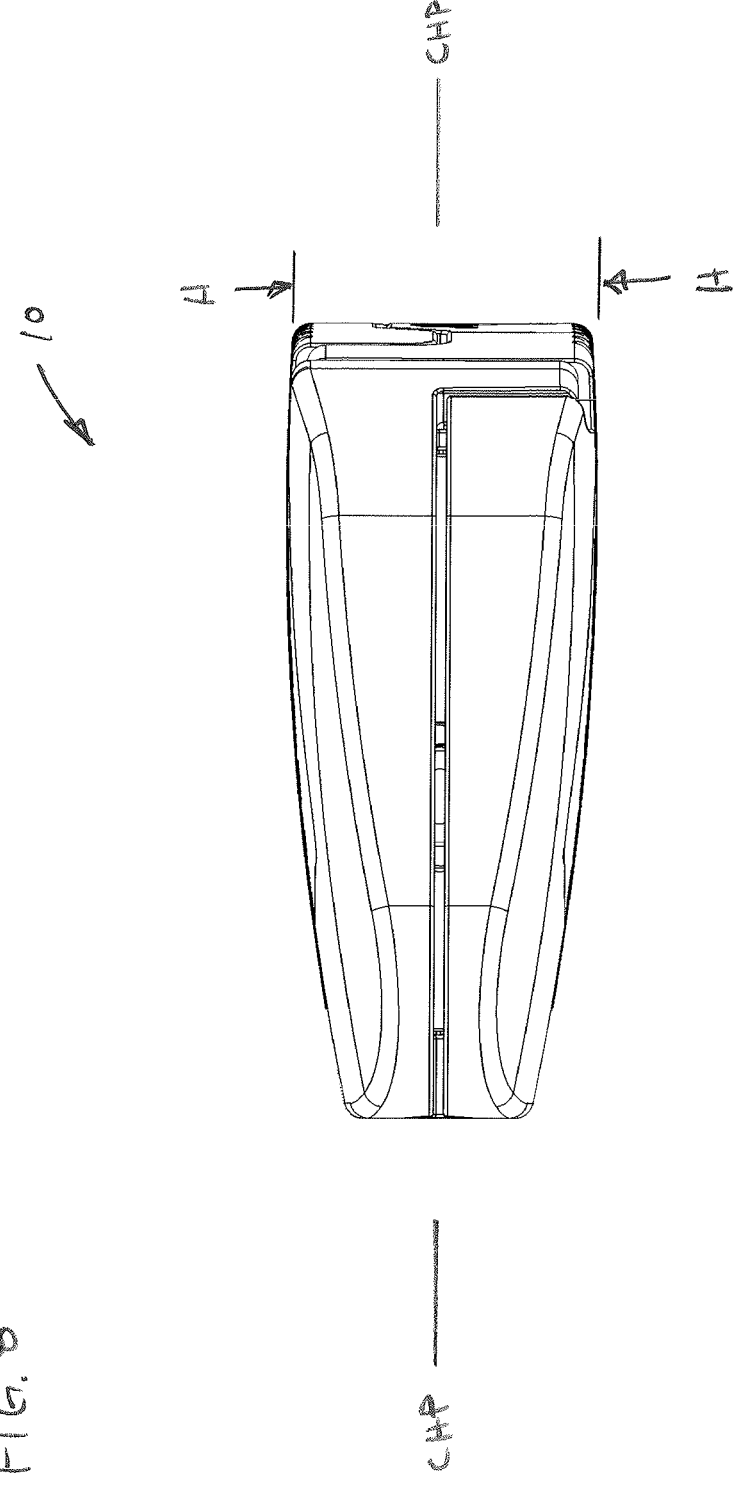
FIG. 8 is a left elevational view of the expandable interbody spacer.

Each of the upper and lower end plates 20, 22 includes an end plate body, 20A, 22A, and opposite posterior and anterior walls 20B, 20C, and 22B, 22C, respectively. The upper and lower end plate bodies 20A, 22A each have an exterior surface configured to engage adjacent vertebra, and an interior surface defining internal components, as explained in more detail below. Each exterior surface of the upper and lower end plate bodies 20, 22 has a knurled, toothed, ribbed, or otherwise non-smooth portion 30, 32 to facilitate frictional engagement and anchoring with the corresponding vertebrae. Each of the upper and lower end plate bodies 20, 22 define a large central opening 34, 36 extending through the exterior and internal surfaces to an interior chamber 38 defined by the opposing end plates 20, 22. As shown in FIGS. 7 and 8, a height H of the interbody spacer 10 defined by the opposite exterior surfaces of the end plate bodies 20, 22 tapers from front (posterior) sides of the end plate bodies toward the rear (anterior) sides of the end plate bodies. Each of the exterior surfaces generally slopes toward a center horizontal plate CHP of the interbody spacer 10 from the front (posterior) sides of the end plate bodies 20, 22 toward the rear (anterior) sides of the end plate bodies.

Figure 3:
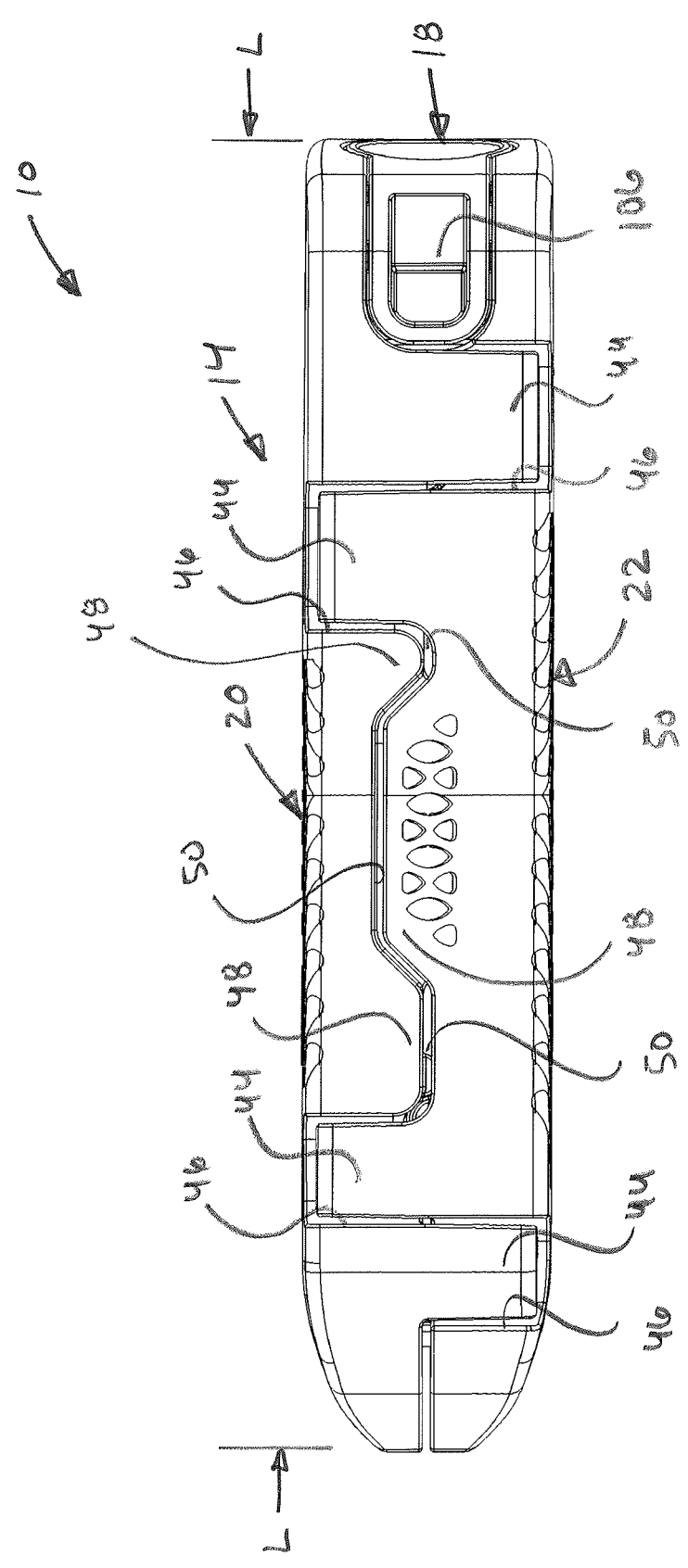
FIG. 3 is a front elevational view of the expandable interbody spacer.
Figure 4:
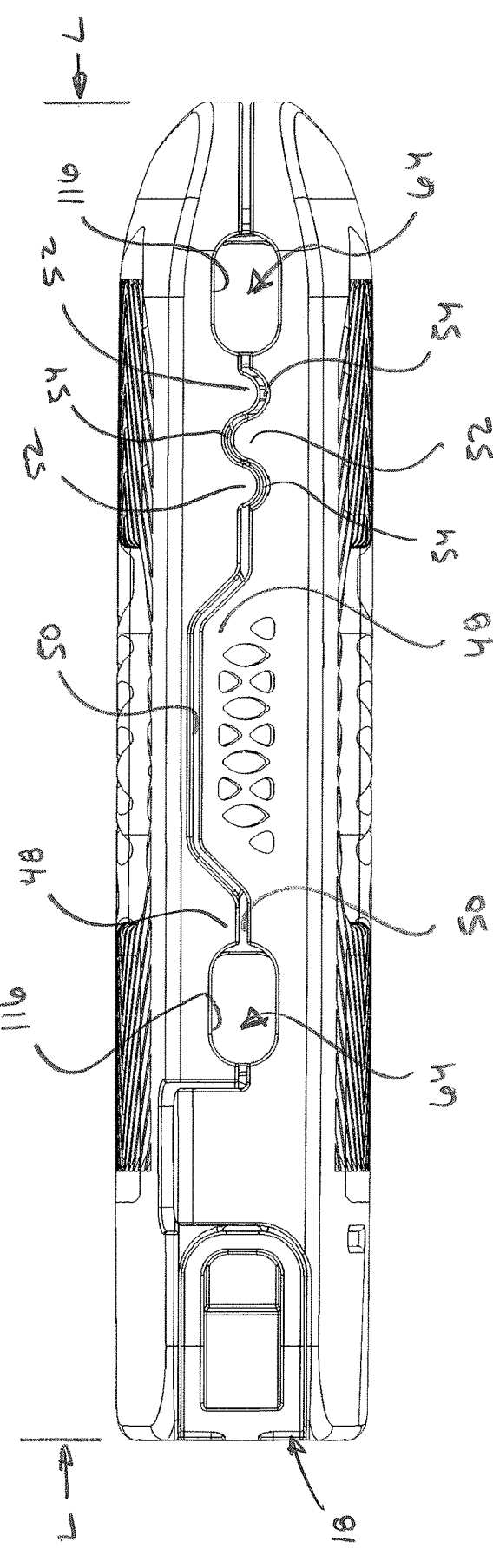
FIG. 4 is a rear elevational view of the expandable interbody spacer.
Figure 5:
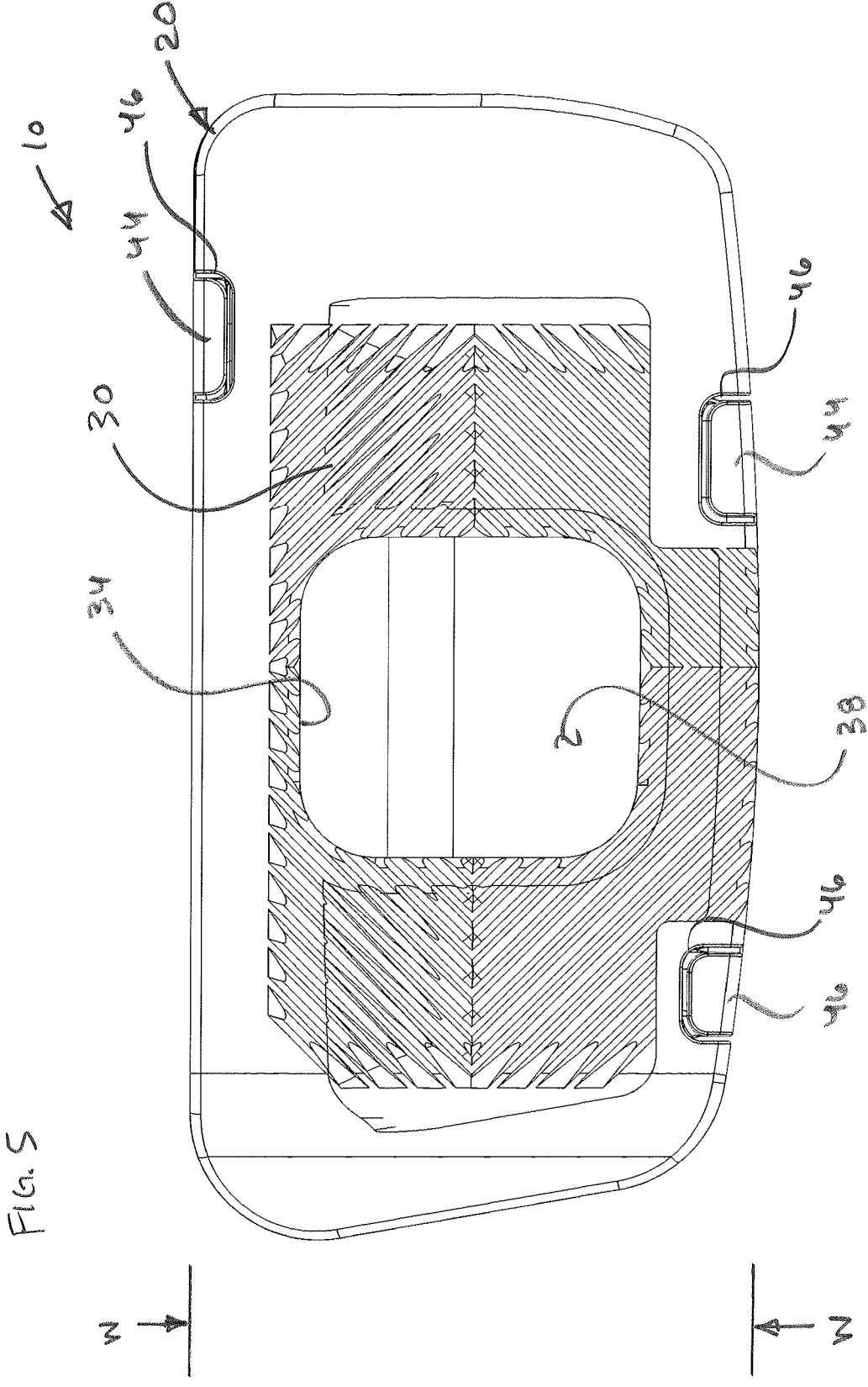
FIG. 5 is a top plan view of the expandable interbody spacer.

As shown in FIGS. 3 and 4, the posterior and anterior walls 20B, 20C, and 22B, 22C of the upper and lower end plates 20, 22 have corresponding elevational shapes such that the walls fully mesh together and interlock when the interbody spacer 10 is collapsed (i.e., non-expanded configuration) and remain interlocked and partially meshed together when the interbody spacer is expanded (i.e., in an expanded configuration). This meshing and interlocking of the corresponding posterior and anterior walls 20B, 20C, and 22B, 22C inhibit shifting of the end plates 20, 22 relative to one another due to shear forces acting upon the end plates. In the illustrated embodiment, each of the posterior and anterior walls 20B, 20C, and 22B, 22C includes at least one tongue 44, 48, 52 and at least one groove (or slot) 46, 50, 54, whereby the tongue(s) of one of the upper and lower end plates 20, 22 is configured to mate with the groove(s) of the other end plate. In the illustrated embodiment, the mating tongue(s) 44, 48, 52 and groove(s) 46, 50, 54 have different shapes (and sizes). For example, a first type of mateable tongue-and-groove interlock has a generally rectangular tongue 44 and rectangular groove 46. In the illustrated embodiment, the posterior walls 20B, 22B of the upper and lower end plates 20, 22 include four such tongue-and-groove interlocks and the anterior walls 22B, 22C include one such tongue-and-groove interlock. As another example, a second type of mateable tongue-and-groove interlock has a tapering, rectilinear tongue 48 and a tapering, rectilinear groove 50. In the illustrated embodiment, the posterior walls 20B, 22B of the upper and lower end plates 20, 22 include four such tongue-and-groove interlocks (one of which is internal and hidden in FIGS. 1 and 2 but shown in FIGS. 9 and 10) and the anterior walls 20C, 22C include three such tongue-and-groove interlocks (one of which is internal and hidden in FIGS. 1 and 2 but shown in FIGS. 9 and 10). As yet another example, a third type of mateable tongue-and-groove interlock has an arcuate tongue 52 and an arcuate groove 54. In the illustrated embodiment, the posterior walls 20B, 22B of the upper and lower end plates 20, 22 do not include such tongue-and-groove interlocks and the anterior walls 20C, 22C include three such tongue-and-groove interlocks.

Figure 16:
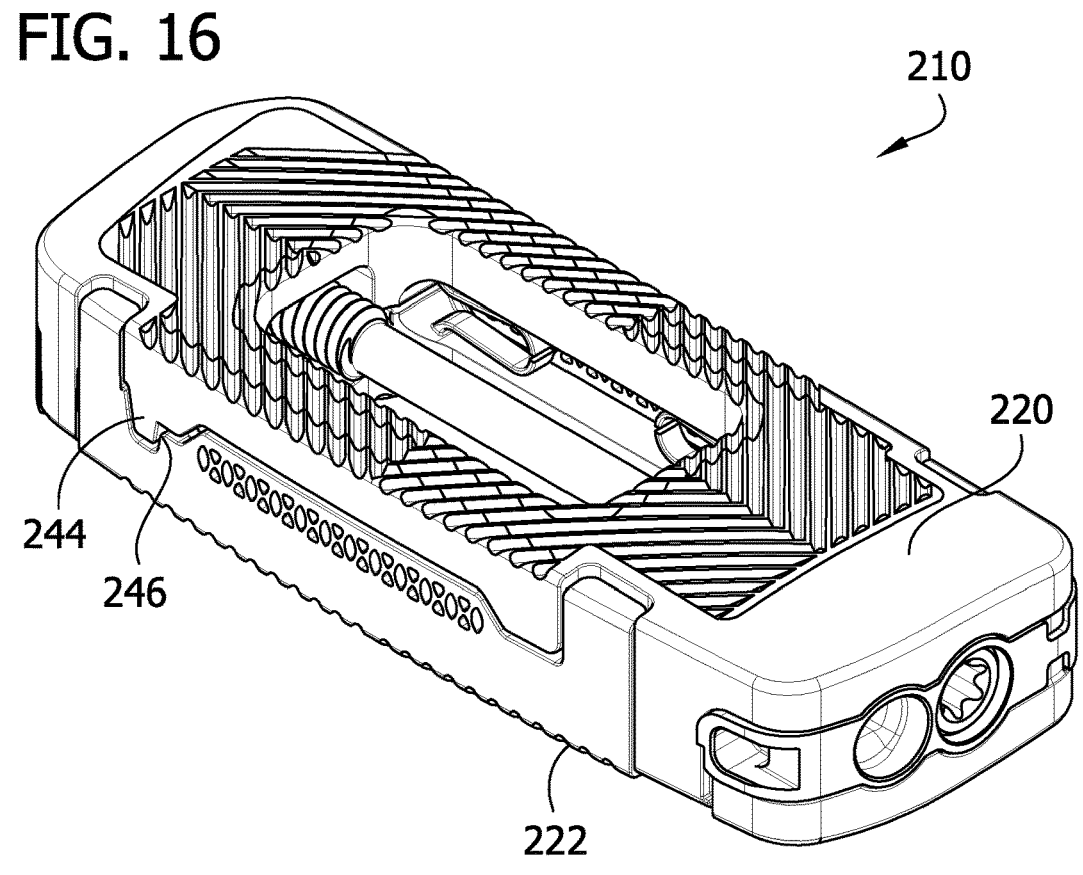
FIG. 16 is a front perspective of another embodiment of an expandable interbody spacer, the interbody spacer being in a collapsed configuration.
Figure 17:
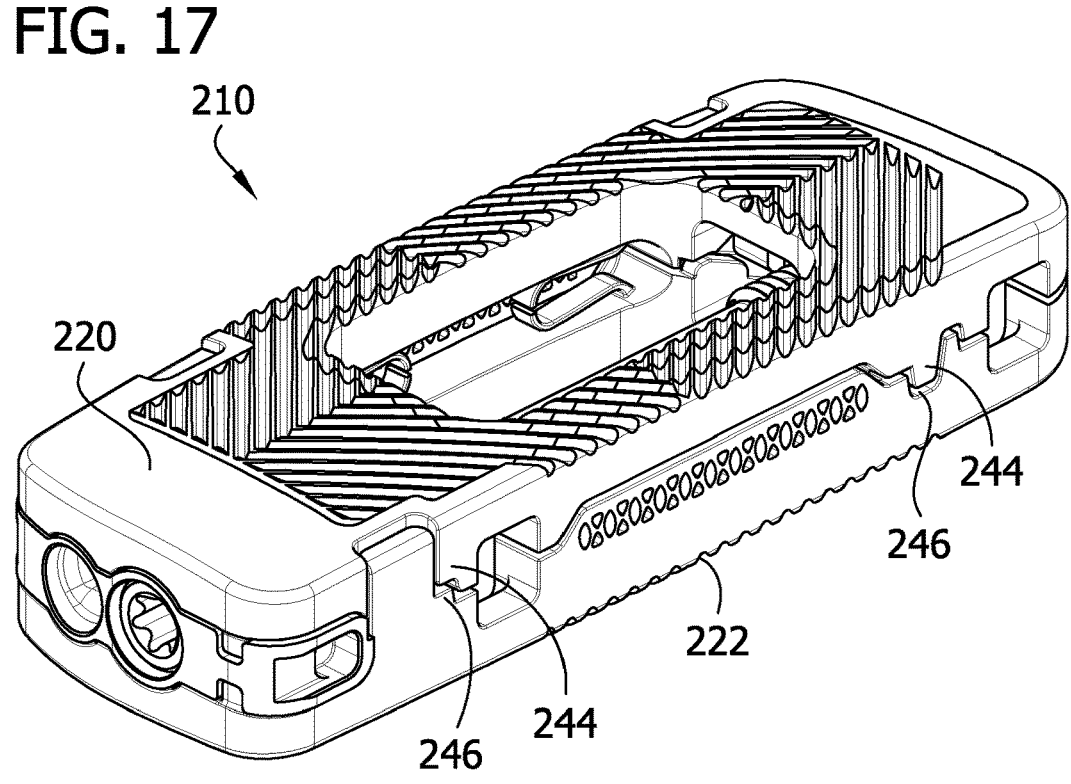
FIG. 17 is a rear perspective of the expandable interbody spacer.

Referring to FIGS. 16 and 17, in another example an expandable interbody spacer 210 includes a tongue-and-groove interlocks that are different than the tongue-and-groove interlocks of the prior embodiment. In this interbody spacer 210, tongues 244 and corresponding grooves 246 have stepped profiles to facilitate interlocking of upper and lower end plates 220, 222 and inhibit relative movement of the end plates due to shearing force. The remaining features of the interbody spacer 210 may be the same or similar to the features of the interbody spacer 10 described herein, and the description of the other features of the interbody spacer 10 apply equally to interbody spacer 210.

Figure 14:
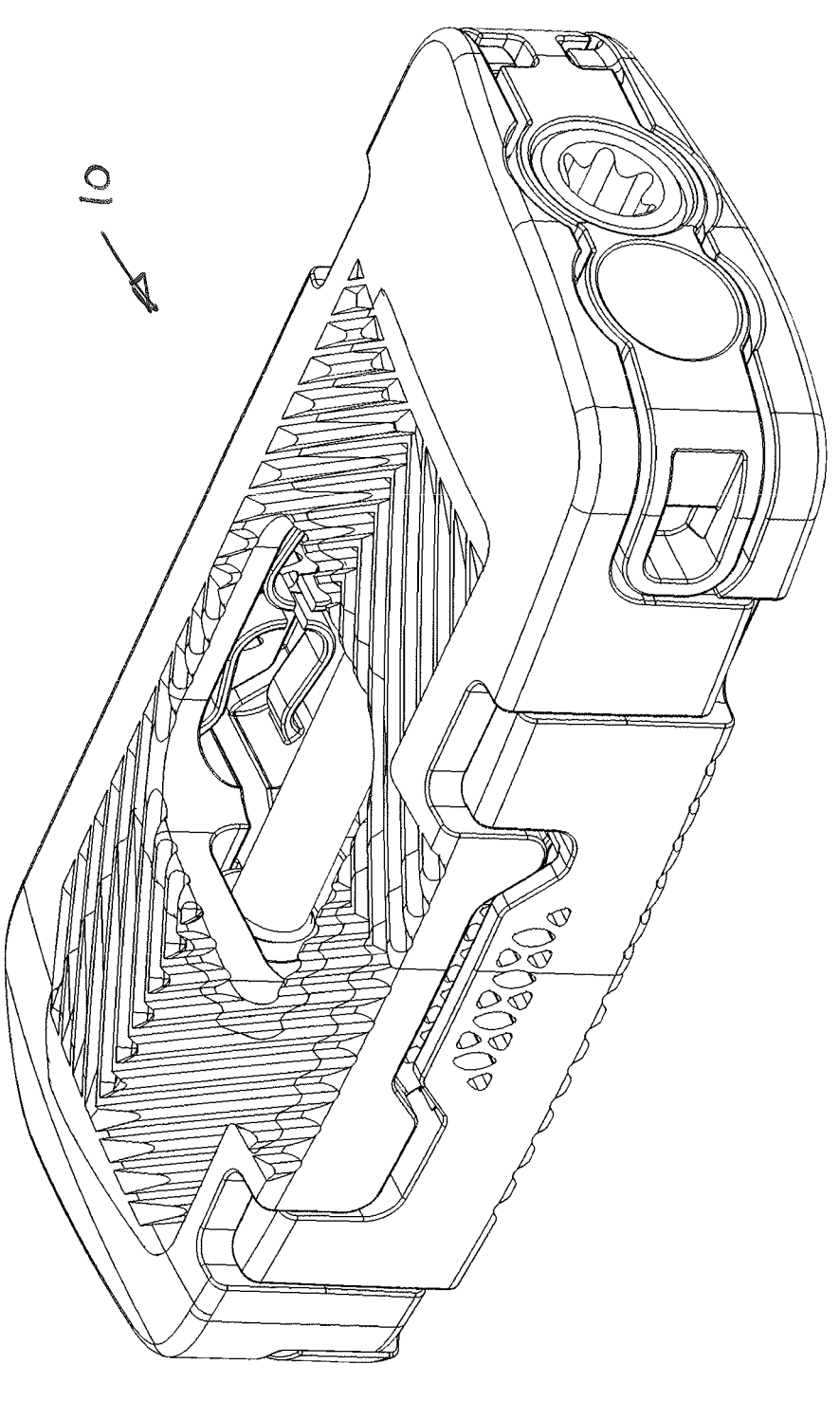
FIG. 14 is a perspective of the interbody spacer in an expanded configuration.
Figure 15:
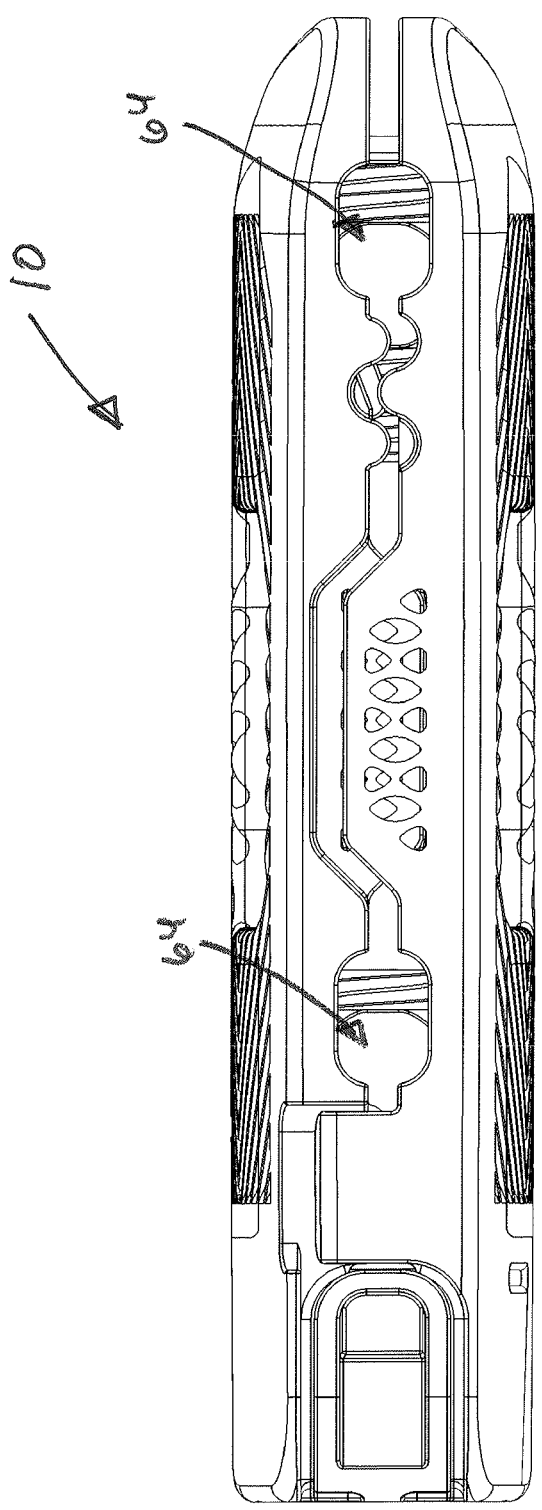
FIG. 15 is a rear elevational view of the expanded interbody spacer.

As described above, the interbody spacer 10 includes internal tongue-and-groove interlocks. In the illustrated embodiment, the lower end plate 22, as shown in FIG. 10, includes internal tongues 48 opposing and overlapping the adjacent tongues of the upper end plate 20, even when the interbody spacer is expanded (as shown in FIGS. 14 and 15). The internal tongues 48 are received in corresponding internal grooves 50 of the upper end plate 20. Through this construction, a central portion of the chamber 38 remains enclosed by the overlapping internal and external tongues 48 when the interbody spacer 10 is collapsed and expanded. These tongues 48 include openings to enable ingrowth and outgrowth of bone. The interbody spacer 10 may include additional internal tongue-and-groove interlocks, including tongues 52 and corresponding grooves 54, as shown in FIGS. 9-12. The internal tongue-and-groove interlocks facilitate stabilization of the interbody spacer 10 and inhibit relative movement of the end plates 20, 22 due to shearing force.

In the illustrated embodiment, the end plate fasteners 24 generally comprise thin strips of material that are resiliently deflectable in the heightwise direction to apply a biasing force to the upper and lower end plates 20, 22, biasing the end plates toward one another. Each end plate fastener 24 is connected directly to and extends between the upper and lower end plates 20, 22. As explained above, in one example, the end plate fasteners 24 are integrally formed with each of the upper and lower end plates 20, 22, such as by additive manufacturing. The end plates fasteners 24 may be the only connections between the two end plates 20, 22 maintaining the end plates in attachment to one another. That is, without the fasteners 24, the end plates 20, 22 are separable from one another. In the illustrated embodiment, each end plate fastener 24 generally comprises a serpentine spring having a single turn, although the springs may have more than one turn in other embodiments. Also in the illustrated embodiment, at least one spring 24 (e.g., two springs) is disposed adjacent the posterior walls 20B, 22B and at least one spring 24 (e.g., two springs) is disposed adjacent the anterior walls 20C, 22C. The springs 24 are disposed within the chamber 38 of the interbody space 10 inward of the corresponding inner tongues 48 of the respective end plates 20, 22. When the spacer casing 14 is expanded in the heightwise direction, the springs 24 expand therewith and apply the biasing force to each of the upper and lower end plates 20, 22. This biasing force helps retain the interbody spacer 10 in the desired expanded state as a unitary body.

Figure 6:
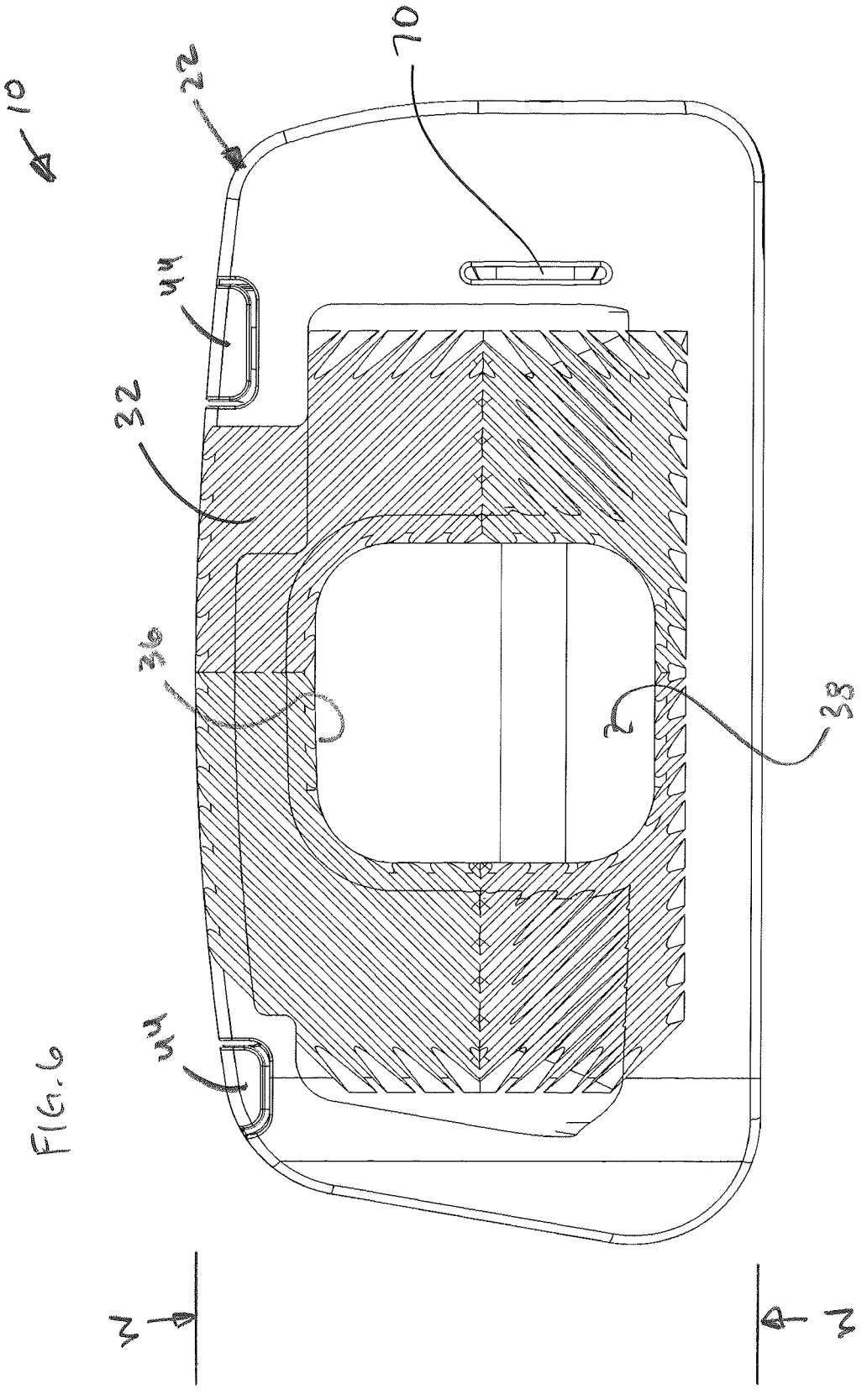
FIG. 6 is a bottom plan view of the expandable interbody spacer.

As shown best in FIGS. 9-12, the illustrated actuator 16 is disposed between the upper and lower end plates 20, 22 and generally includes a rotatable screw drive, generally indicated at reference numeral 60, and at least one barrel nut (e.g., two barrel nuts), generally indicated at reference numeral 64, threaded on the screw drive and translatable longitudinally on the screw drive. The screw drive 60 extends lengthwise (i.e., in the medial/lateral direction) between the upper and lower end plates 20, 22. The illustrated screw drive 60 is laterally offset from a central longitudinal axis of the interbody spacer 10. The screw drive 60 includes a head 66 rotatably coupled to the coupling at the lateral (trailing) end of the interbody spacer 10. The head 66 includes a socket or other coupler for receiving a tool (e.g., a head of a screwdriver) to impart rotation of the screw drive 60 relative to the spacer casing 14, the coupling 18, and the barrel nuts 64. The illustrated screw drive 60 includes a threaded shaft 68 extending from the head 66 to adjacent the medial (leading) end of the interbody spacer 10. The illustrated shaft 68 includes longitudinally spaced apart threaded portions, one adjacent the medial (leading) end and the other adjacent the lateral (trailing) end of the interbody spacer 10, such that a central portion of the shaft is unthreaded and smooth. The location of the unthreaded portion generally coincides with the upper and lower central openings 34, 36 of the upper and lower end plates 20 22 to facilitate packing of bone graft in the chamber 38 and to inhibit disturbing the packed bone graft when rotating the screw drive 60. A retaining ring (not shown) coupled to the screw drive 60 retains the screw drive in position and inhibits the screw drive from withdrawing from the coupling 18 and the spacer casing 14. The retaining ring is inserted and clipped onto the screw drive 60 through a slot 70 (FIG. 6) in the lower end plate 22 (or the upper end plate 20).

Figure 13:
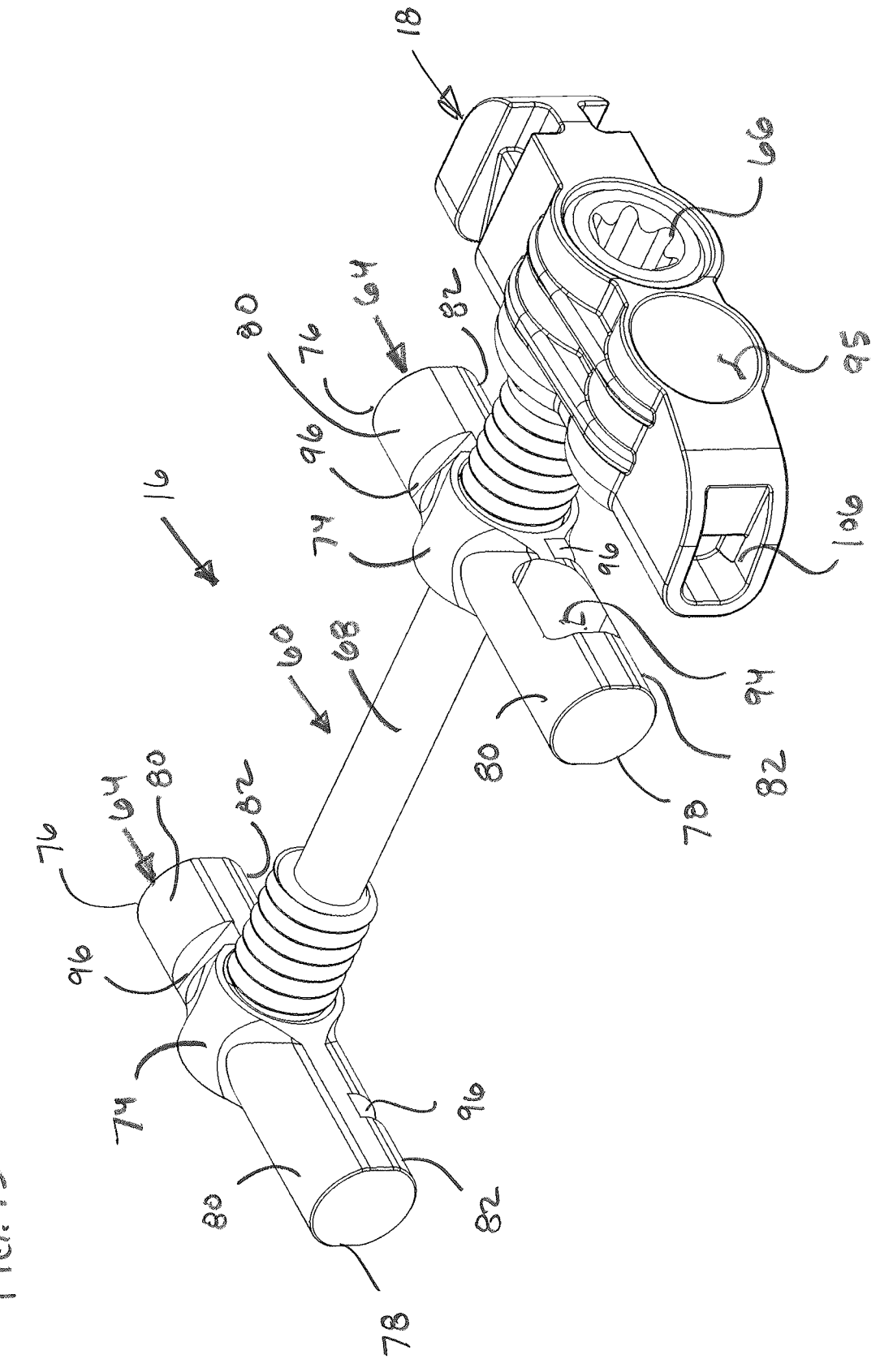
FIG. 13 is a perspective of the actuator and coupling.

Two longitudinally spaced barrel nuts 64 are present in the illustrated embodiment: a medial (leading) barrel nut and a lateral (trailing) barrel nut. Each barrel nut 64 has a length extending generally transverse to the screw drive, such as in the anterior/posterior direction. An internally threaded portion 74 of each barrel nut 64 threadably receives the corresponding threaded portion 68 of the screw drive 60. Each internally threaded portion 68 is off-center of the length of the barrel nut 64. As seen best in FIG. 13, each barrel nut 64 further includes first and second longitudinal portions 76, 78, respectively, on opposite sides of the internally threaded portion 74. Each of these longitudinal portions include upper and lower ramp engagement surfaces 80, 82, respectively, of the barrel nut 64 which engage and ride along upper and lower internal ramps 90, 92, respectively, on or defined by the interior surfaces of the corresponding upper and lower end plate bodies 20A, 22A when the drive screw 60 is rotated, thereby imparting expansion of the spacer casing 14 in the heightwise direction. In the illustrated embodiment, the second longitudinal portions 78 of the barrel nuts 64 are longer than the first longitudinal portions 76. Moreover, the lateral (trailing) barrel nut 64 (e.g., the second longitudinal portion thereof 78) defines a window 94 to enable bone graft to inserted therethrough and into the chamber 38 of the interbody spacer 10. The window 94 is generally aligned with a passage 95 extending through the coupling 18, which enables the bone graft to be inserted and packed in the interbody spacer 10.

The upper and lower ramp engagement surfaces 80, 82 are generally rounded (i.e., arcuate) such that the first and second longitudinal portions have generally cylindrical shapes. The illustrated longitudinal portions 76, 78 have flat surfaces side surface between the upper and lower ramp engagement surfaces 80, 82, which may engage internal stops (e.g., internal shoulder or other surface of the interior surfaces) within the spacer casing 14 to restrict a distance the barrel nuts 64 are translatable on the screw drive 60. The illustrate barrel nuts 64 define slots 96 which receive ribs 98 on or defined by the interior surfaces of the corresponding upper and lower end plate bodies 20, 22. The slots 96 and ribs 98 provide proper tracking of the barrel nuts 64 as they translate along the screw drive 60 when the screw drive is rotated. The slots 96 and ribs 98 also inhibit the screw drive 60 from imparting rotation of the barrel nuts 64 to limit lost translational movement of the barrel nuts as the screw drive is rotated.

Figure 9:
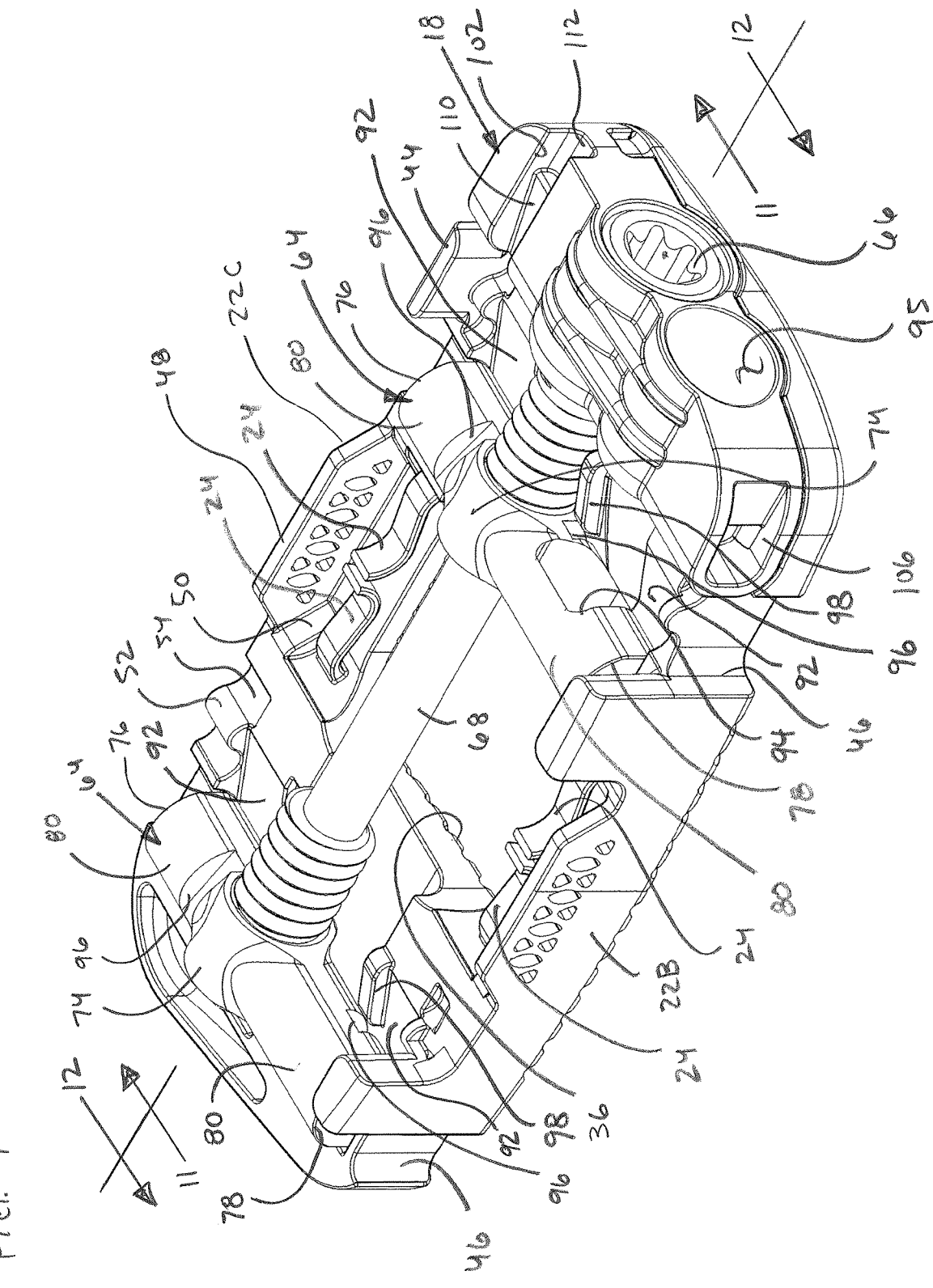
FIG. 9 is a top perspective of a lower end plate, actuator, and coupling of the interbody spacer.
Figure 10:
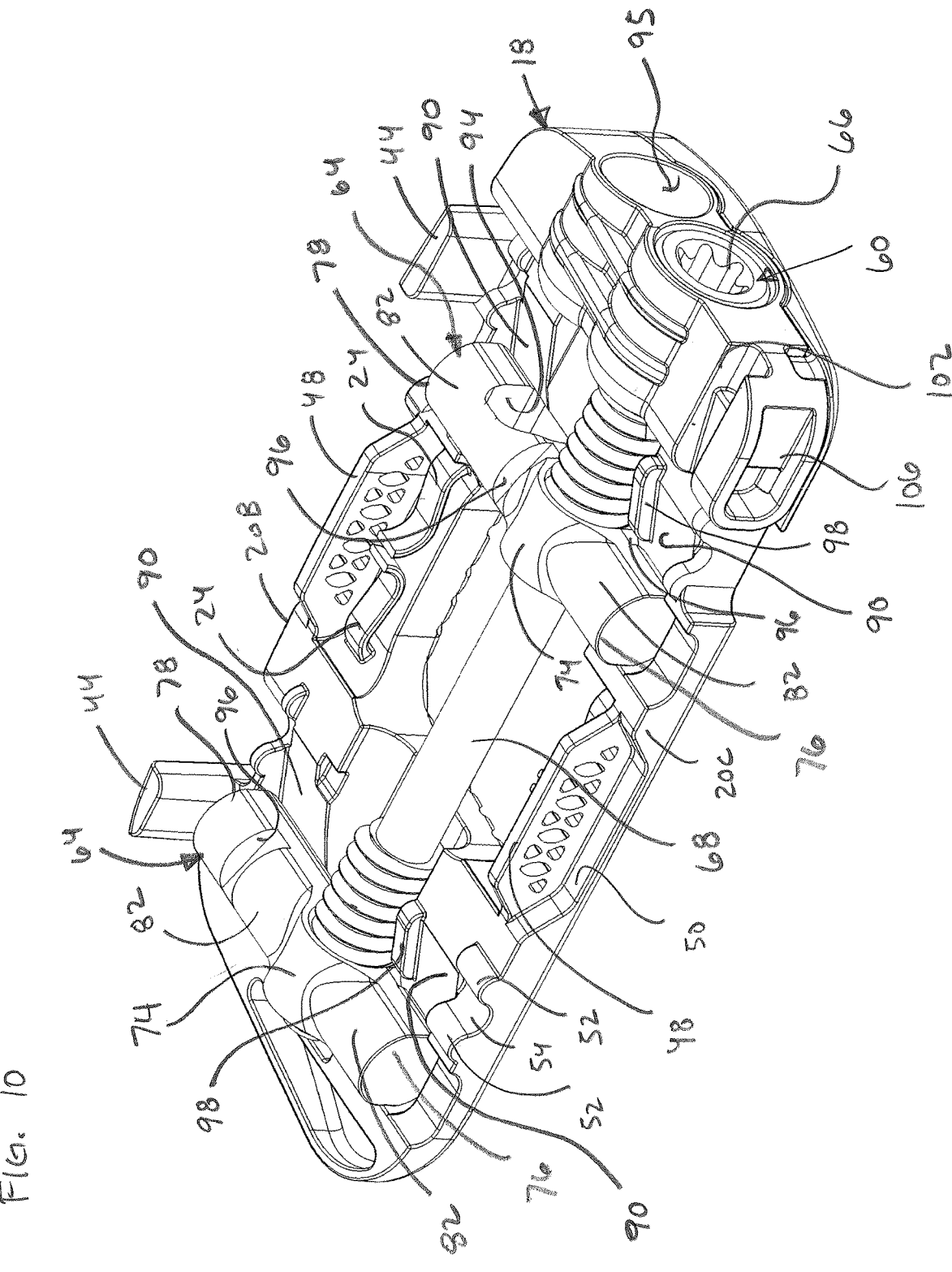
FIG. 10 bottom perspective of an upper end plate and the actuator and the coupling of the interbody spacer.

As shown best in FIGS. 9 and 10, for example, the coupling 18 is disposed between the upper and lower end plates 20, 22 at the lateral (trailing) end of the interbody spacer 10. As described above, the drive screw 60 is received in and rotatable within the coupling 18. The socket 66 of the drive screw 60 is accessible to a practitioner for receiving a tool head to actuate rotation of the drive screw. Accordingly, the coupling 18 functions as a bearing for the rotatable drive screw 60. The illustrated coupling 18 further defines upper and lower slots 102 which receive corresponding interlocking tabs 104 on the upper and lower end plate bodies 20, 22. The interlocking tabs 104 are fully received in the corresponding slots 102 when the interbody spacer 10 is collapsed, and the interlocking tabs 104 may remain partially within the slots 102 as the interbody spacer is expanded.

Through the arrangement, the coupling 18 is inhibited from rotating or translating relative to the upper and lower end plates 20, 22, both as the drive screw 60 is rotated and the interbody spacer 10 is expanded and when the interbody spacer is static (i.e., not rotating).

The coupling 18 further includes coupler recesses 106 at posterior and anterior sides of the coupling. The coupler recesses 106 are configured to removably receive and releasably couple with fingers on a suitable inserter for the interbody spacer 10. Such an inserter (not shown) would also include the drive (e.g., screw driver) that mates with the socket 66 of the drive screw 60 and actuates rotation of the drive screw to impart expansion of the interbody spacer 10. The interbody spacer 10 may have another type of connection for mating with a suitable inserter.

Figure 11:
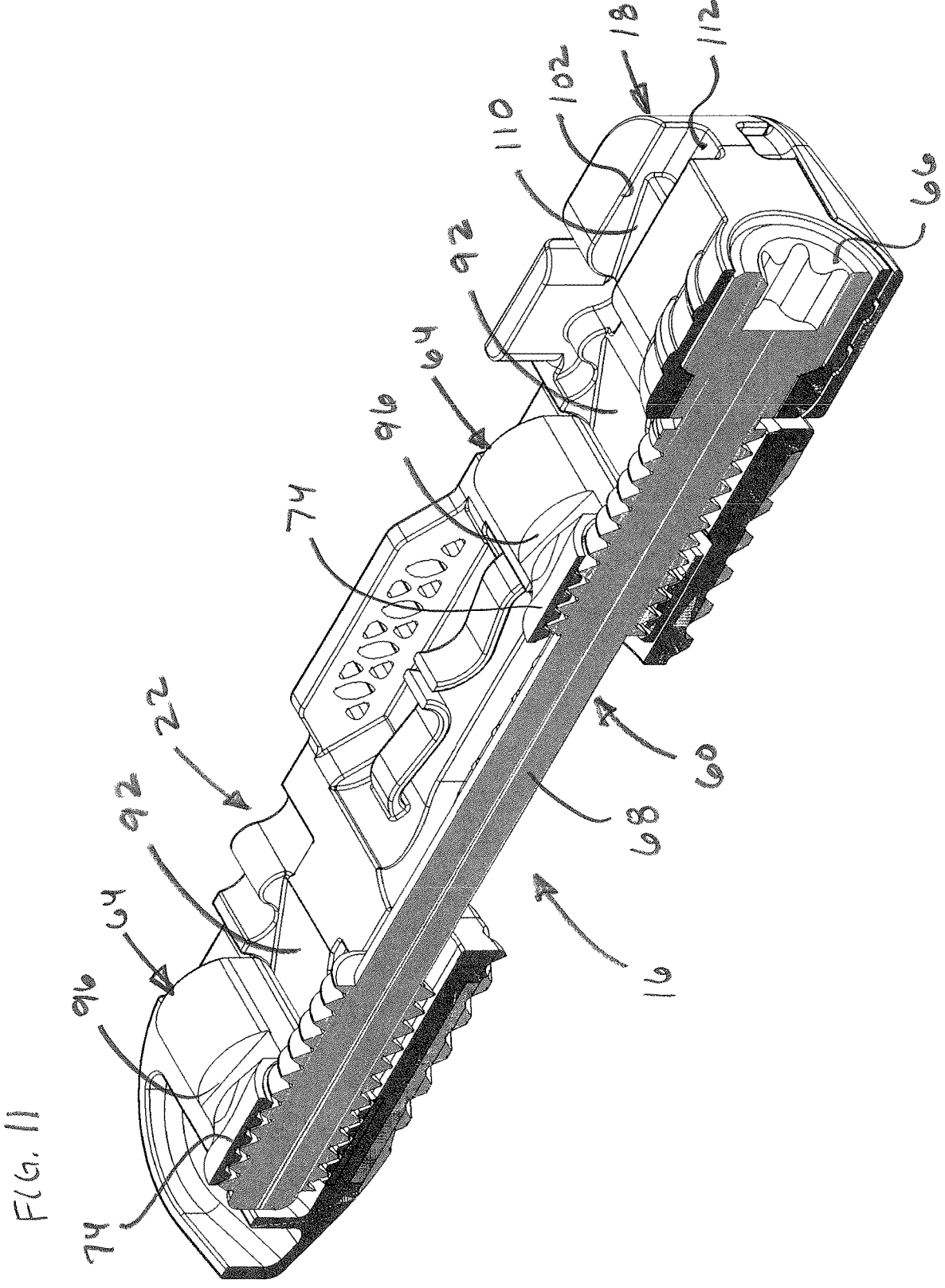
FIG. 11 is a cross section of FIG. 9 as indicated by arrows 11.
Figure 12:
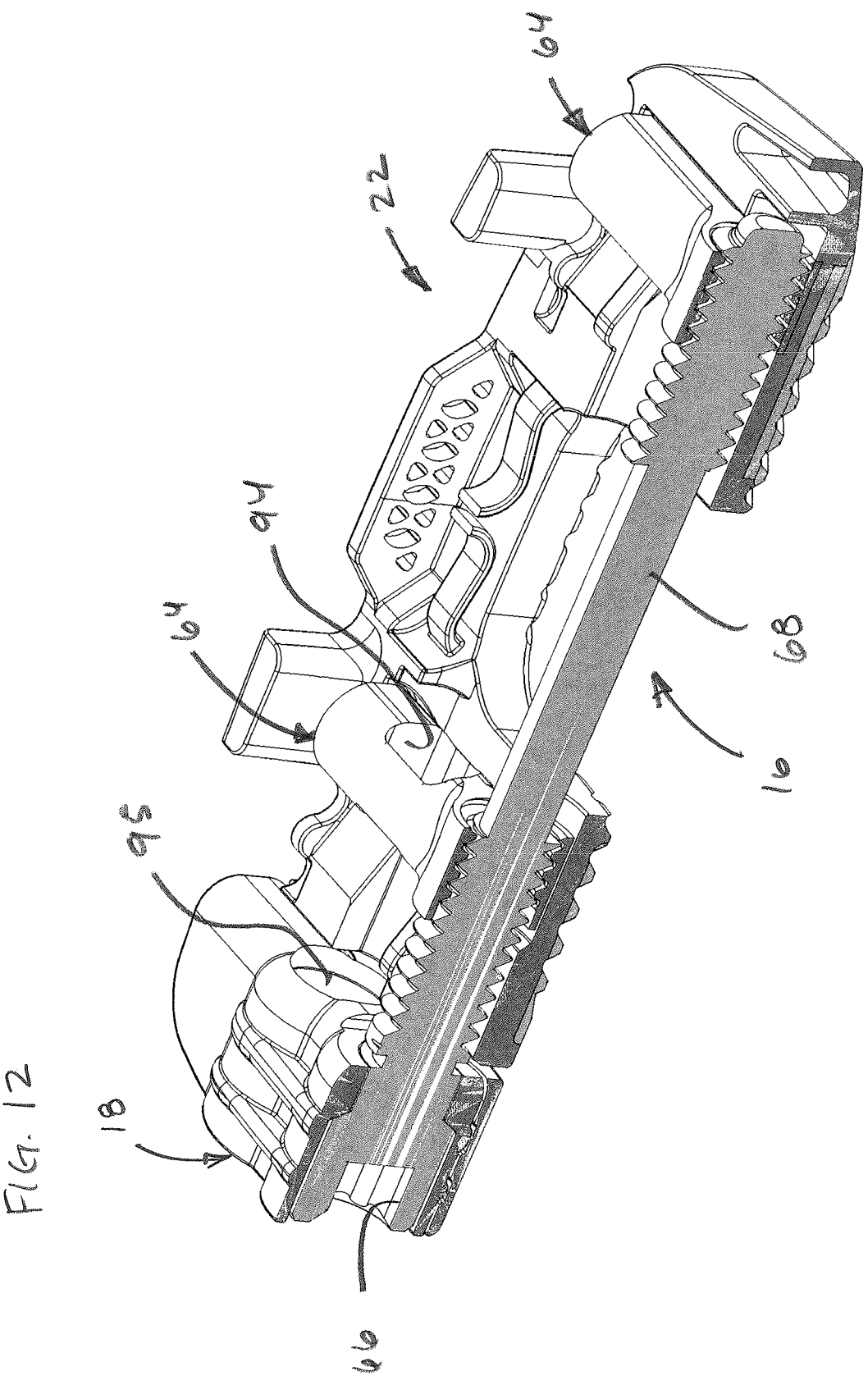
FIG. 12 is a cross section of FIG. 9 as indicated by arrows 12.

In one embodiment, the interbody spacer 10 may be easily assembled in a few steps, mainly due to the spacer casing 14 (e.g., the end plates 20, 22 and the end plate fasteners 24) being formed by additive manufacturing as a single, one-piece, monolithic component. In particular, the spacer casing 14 may be integrally formed during additive manufacturing to include each of the upper and lower end plates 20, 22 (including the internal components and structures—such as the tongues and grooves, the internal ramps, the internal ribs, etc. —) and the end plate fasteners 24. With this structure formed, the coupling 18 and the actuator 16 are then secured to the spacer casing 14. For example, as seen in FIG. 11, the coupling 18 may be attached to spacer casing 14 by sliding the coupling between the upper and lower end plates 20, 22, whereupon the interlocking tabs 104 enter the slots 102 of the coupling, ride along ramps 110 within the slots, and then drop down into enlarged recesses 112, thereby locking onto the spacer casing (e.g., snap-locking). The barrel nuts 64 can be slid through openings 116 defined by the walls (e.g., anterior walls 20C, 22C) of the upper and lower end plates 20, 22 and into interior recesses defined by the interior surfaces of the upper and lower end plates. The screw drive 60 is then inserted through the coupling 18 and threaded into the barrel nuts 64 in the spacer casing 14, after which the retaining ring (not shown) is inserted into the slot 75 and secured around the shaft 68 of the drive screw 60 to inhibit the drive screw from withdrawing from the spacer casing. With these minimal steps, the interbody spacer 10 is fully assembled.

In an exemplary use, the interbody spacer 10 in its collapsed configuration is inserted between adjacent vertebra during a surgical procedure, such as LLIF or XLIF procedure. The medial (leading) end of the interbody spacer 10 is inserted first, leaving the lateral (trailing) end accessible. A suitable inserter (not shown) may be used, as described above. After insertion and placement, the interbody spacer 10 may be expanded a suitable and desired height using a drive tool (e.g., screw driver), which may be associated with the inserter, as it generally known in the field. Rotation of the drive tool imparts rotation of the drive screw 60 about its axis relative to the spacer casing 14. As the drive screw 60 rotates, the barrel nuts 64 translate along the drive screw toward the head 66 of the drive screw (e.g., toward the lateral (trailing) end of the interbody spacer 10). During translation, the upper and lower ramp engagement surfaces 80, 82 of the barrel nuts 64 ride along the corresponding upper and lower internal ramps 90, 92, thereby moving the upper and lower end plates 20, 22 away from one another in the heightwise direction to expand the spacer casing 14. The screw drive 60 is rotated (and the barrel nuts 64 are translated) a suitable amount to obtain the desired heightwise expansion of the interbody spacer 10, which corresponds with a desired movement and spacing of the adjacent vertebra. Once the desired expansion is reached, bone graft may be packed in the interbody spacer 10 by inserting the graft material into the passage 95 of the coupling 18, through the window 94 of the trailing barrel nut 64, and into the central portion of the chamber 38 at the central openings 34, 36 of the end plates 20, 22. As described above, the overlapping walls (or tongues 48) adjacent the central openings 34, 36 help enclose the graft material and inhibit the material from falling out the sides of the interbody spacer 10. Moreover, the openings in the walls (or tongues 48) allow for bone ingrowth and outgrowth to facilitate fusion.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed:

1. An expandable interbody spacer for spinal fusion, the expandable interbody spacer comprising:

upper and lower end plates opposing one another and defining an internal chamber therebetween sized to receive bone graft therein, each of the upper and lower end plates including an end plate body and opposite posterior and anterior walls at corresponding posterior and anterior sides of the end plate body, wherein a distance between the upper and lower end plate bodies defines a height of the expandable interbody spacer;

an actuator disposed between the upper and lower end plates, the actuator configured to move the upper and lower end plates heightwise relative to one another to expand the height of the expandable interbody spacer and configure the expandable interbody spacer between a collapsed configuration and an expanded configuration; and at least one end plate fastener securing the upper and lower end plates to one another and enabling the upper and lower end plates to move heightwise relative to one another, wherein the upper and lower end plates and the at least one end plate fastener are integrally formed as a single, one-piece, monolithic component, wherein each of the posterior walls of the upper and lower end plates includes tongues and grooves mating with corresponding tongues and grooves of the other posterior wall in the collapsed configuration, and wherein each of the anterior walls of the upper and lower end plates includes tongues and grooves mating with corresponding tongues and grooves of the other anterior wall in the collapsed configuration, wherein the tongues of the posterior walls of the upper and lower end plates overlap one another in an anterior-poster direction when the expandable interbody spacer is in the collapsed and expanded configurations, and wherein the tongues of the anterior walls of the upper and lower end plates overlap one another in an anterior-poster direction when the expandable interbody spacer is in the collapsed and expanded configurations, wherein the at least one fastener is disposed between the anterior and posterior walls in the anterior-posterior direction.

2. The expandable interbody spacer of claim 1, wherein the at least one end plate fastener comprises a tension spring biasing the upper and lower end plates toward one another.

3. The expandable interbody spacer of claim 2, wherein the spring is a serpentine spring.

4. The expandable interbody spacer of claim 1, wherein the at least one end plate fastener comprises at least two end plate fasteners.

5. The expandable interbody spacer of claim 1, wherein the actuator includes a drive screw including a threaded portion, the drive screw being selectively rotatable about its axis, and at least one barrel nut comprising an internally threaded portion threaded on the screw drive, wherein rotation of the drive screw imparts translation of the at least one barrel nut along the drive screw and relative to the upper and lower implants to impart heightwise movement of the upper and lower end plates relative to one another.

6. The expandable interbody spacer of claim 5, wherein the at least one barrel nut comprises at least two barrel nuts.

7. The expandable interbody spacer of claim 5, wherein the at least one barrel nut includes a first longitudinal portion and a second longitudinal portion, wherein the internally threaded portion is disposed between the first and second longitudinal portions, wherein the first longitudinal portion defines a window to enable bone graft to pass therethrough and into the internal chamber.

8. The expandable interbody spacer of claim 7, wherein the first longitudinal portion has a length greater than a length of the second longitudinal portion.

9. The expandable interbody spacer of claim 8, wherein the axis of the drive screw is laterally offset from a central longitudinal axis of the interbody spacer.

10. The expandable interbody spacer of claim 6, wherein the drive screw includes two of the threaded portions and a non-threaded portion disposed between threaded portions, wherein the non-threaded portion is disposed in the internal chamber.

11. The expandable interbody spacer of claim 1, wherein the posterior and anterior walls of the lower plate define openings therethrough and in communication with the internal chamber to enable bone growth.

12. The expandable interbody spacer of claim 1, wherein the upper and lower end plates and the at least one end plate fastener are integrally formed as a single, one-piece, monolithic component by additive manufacturing.

13. An expandable interbody spacer for spinal fusion, the expandable interbody spacer comprising:

upper and lower end plates opposing one another and defining an internal chamber therebetween sized to receive bone graft therein, each of the upper and lower end plates including an end plate body and opposite posterior and anterior walls at corresponding posterior and anterior sides of the end plate body, wherein a distance between the upper and lower end plate bodies plates defines a height of the expandable interbody spacer;

an actuator disposed between the upper and lower end plates, the actuator configured to move the upper and lower end plates heightwise relative to one another to expand the height of the expandable interbody spacer, wherein the actuator comprises:

a drive screw including a threaded portion, the drive screw being selectively rotatable about its axis;

at least one barrel nut comprising an internally threaded portion threaded on the screw drive, wherein rotation of the drive screw imparts translation of the at least one barrel nut along the drive screw and relative to the upper and lower implants to impart heightwise movement of the upper and lower end plates relative to one another, wherein the at least one barrel nut includes a first longitudinal portion and a second longitudinal portion, wherein the internally threaded portion is disposed between the first and second longitudinal portions, the first longitudinal portion defining a window to enable bone graft to pass therethrough and into the internal chamber;

a coupling coupled to the drive screw to enable rotation of the drive screw relative to the coupling, wherein the coupling defines a passage therethrough, the passage being generally aligned with the window defined by the barrel nut to enable bone graft to pass through the passage to the window; and at least one end plate fastener securing the upper and lower end plates to one another and enabling the upper and lower end plates to move heightwise relative to one another, wherein the at least one fastener is disposed between the anterior and posterior walls in the anterior-posterior direction.

14. The expandable interbody spacer of claim 13, wherein the first longitudinal portion has a length greater than a length of the second longitudinal portion.

15. An expandable interbody spacer for spinal fusion, the expandable interbody spacer comprising:

upper and lower end plates opposing one another and defining an internal chamber therebetween sized to receive bone graft therein, each of the upper and lower end plates including an end plate body and opposite posterior and anterior walls at corresponding posterior and anterior sides of the end plate body, wherein a distance between the upper and lower end plate bodies defines a height of the expandable interbody spacer;

an actuator disposed between the upper and lower end plates, the actuator configured to move the upper and lower end plates heightwise relative to one another to expand the height of the expandable interbody spacer and configure the expandable interbody spacer between a collapsed configuration and an expanded configuration; and at least one end plate fastener securing the upper and lower end plates to one another and enabling the upper and lower end plates to move heightwise relative to one another, wherein the at least one fastener is disposed between the anterior and posterior walls in the anterior-posterior direction, wherein the anterior walls of the upper and lower end plates include anterior overlapping portions that overlap one another and are in opposing relationship to one another in an anterior-posterior direction when the expandable interbody spacer is in the collapsed and expanded configurations, wherein the posterior walls of the upper and lower end plates include posterior overlapping portions that overlap one another and are in opposing relationship to one another in the anterior-posterior direction when the expandable interbody spacer is in the collapsed and expanded configurations, wherein each of the anterior and posterior walls of the lower end plate define openings therethrough and in communication with the internal chamber to enable bone growth.

16. The expandable interbody spacer set forth in claim 15, wherein the anterior and posterior overlapping portions comprise tongues, wherein the tongues are received in corresponding grooves defined by the posterior and anterior walls of the upper and lower end plates.

\*　　\*　　\*　　\*　　\*